(12) United States Patent
Baer

(10) Patent No.: US 7,642,536 B2
(45) Date of Patent: Jan. 5, 2010

(54) REAL-TIME HIGH-MAGNIFICATION STEREOSCOPIC MICROSCOPE

(76) Inventor: Stephen C. Baer, 10 Poplar Rd., Cambridge, MA (US) 02138

( * ) Notice: Subject to any disclaimer, the term of this patent is extended or adjusted under 35 U.S.C. 154(b) by 0 days.

(21) Appl. No.: 11/795,324

(22) PCT Filed: Jan. 17, 2006

(86) PCT No.: PCT/US2006/001959

§ 371 (c)(1), (2), (4) Date: Jul. 16, 2007

(87) PCT Pub. No.: WO2006/078856

PCT Pub. Date: Jul. 27, 2006

(65) Prior Publication Data

US 2008/0135790 A1   Jun. 12, 2008

Related U.S. Application Data

(60) Provisional application No. 60/644,629, filed on Jan. 16, 2005.

(51) Int. Cl.
*G01N 23/04* (2006.01)
(52) U.S. Cl. .................................... 250/584
(58) Field of Classification Search ............ 250/584, 250/309
See application file for complete search history.

(56) References Cited

U.S. PATENT DOCUMENTS

| | | | |
|---|---|---|---|
| 3,547,512 A * | 12/1970 | Baer | ............ 359/226 |
| 6,259,104 B1 | 7/2001 | Baer | |
| 6,444,476 B1 | 9/2002 | Morgan | |
| 6,563,113 B1 | 5/2003 | Amann et al. | |
| 6,903,347 B2 | 6/2005 | Baer | |
| 7,161,656 B2 | 1/2007 | Neil et al. | |

OTHER PUBLICATIONS

Jaroszewicz, J., et al. Programmable axicon for variable inclination of the focal segment., J. Mod. Opt., 2004, p. 2185-2190, v. 51, Taylor and Francis. UK.
McLeod, J. The axicon: a new type of optical element. J. Op. Soc. Am., 1954, p. 592-597. v. 44. Opt. Soc. Am. US.

* cited by examiner

*Primary Examiner*—David P Porta
*Assistant Examiner*—Kiho Kim

(57) ABSTRACT

A microscope produces a high magnification stereoscopic image of a specimen by generating in the specimen two needle shaped illuminated regions tilted in optical axis of the microscope using a plurality of pinholes, moveable mirrors, and beamsplitters (37, 70). Light emitted from the needle shaped regions is detected using separate detectors (56, 57). The needle shaped regions are scanned with respect to the specimen using scanner (3). Alternately, a hologram may be used to generate the needle shaped illuminated regions.

20 Claims, 5 Drawing Sheets

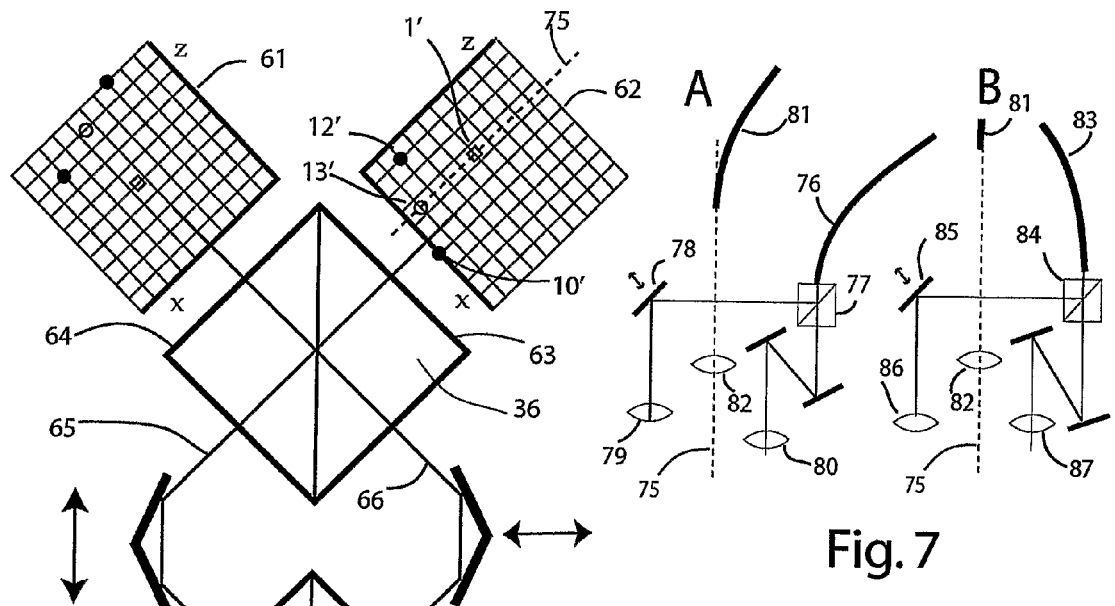
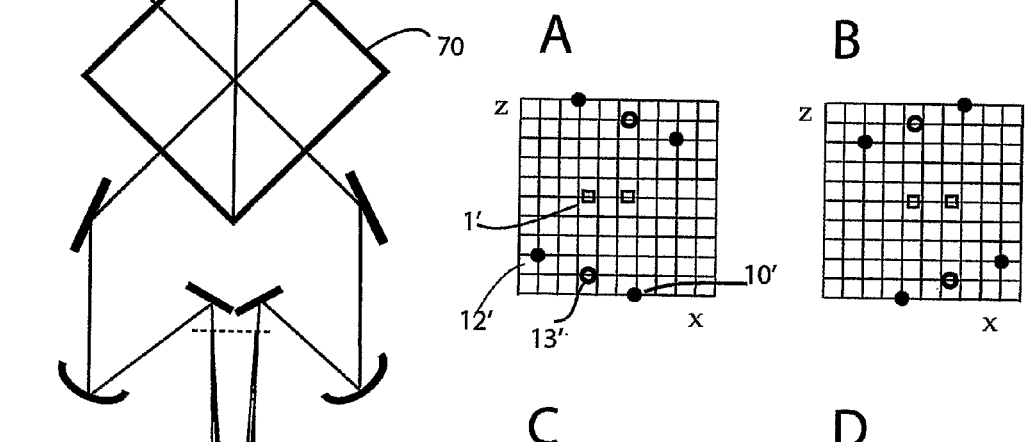
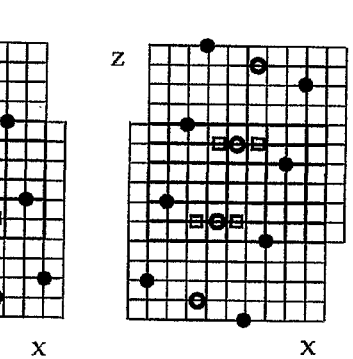
Fig. 6
Fig. 7
Fig. 8

US 7,642,536 B2

REAL-TIME HIGH-MAGNIFICATION STEREOSCOPIC MICROSCOPE

CROSS REFERENCE TO RELATED APPLICATION

This application claims priority from U.S. Provisional Patent Application Ser. No. 60/644,629, filed Jan. 16, 2005, the entire disclosure of which is hereby incorporated by reference.

FIELD OF THE INVENTION

The present invention relates to scanned optical systems, and in particular to microscopes, and more specifically to improvements in depth-enhanced and stereoscopic imaging.

BACKGROUND OF THE INVENTION

A long standing problem in light microscopy is how to generate real time stereoscopic images at high magnifications. At low magnifications, where it is simple to provide appropriate left eye and right images for improved depth discrimination, stereoscopic visualization is almost always the preferred imaging mode in applications such as dissection, microsurgery and microassembly. However at higher magnifications, where such depth discrimination could be just as useful in some applications, stereoscopic imaging is very rarely used, in part because of the unavailability of a simple method that does not add a considerable delay to the imaging process. One partial solution has been to occlude opposite halves of the exit pupils of the left and right eyepieces, which creates an illusion of stereopsis, but with a resulting reduced resolution, and no solution of the depth-of-field problem. Another proposed solution has involved projecting the primary real image of a high power microscope onto a surface that was rapidly scanned in depth, and to visualize the light reflected from that surface with a low power dissecting microscope. This caused a substantial light loss, image degradation, and a magnification that changed with depth. Proposals have been made for real time, high magnification stereoscopic visualization, for example by introducing deliberate longitudinal chromatic aberration during confocal imaging, and applying opposite lateral chromatic dispersion to the images for the left and right eyes (Baer, U.S. Pat. No. 3,547,512), however this process cannot work with fluorescence imaging or with monochromatic laser illumination. One technique for producing stereoscopic image pairs that works with confocal imaging is to create a stack of images at different, closely spaced depths, and make two stacks of summated images, one for the right eye where before summation, each image is shifted lateral in one direction by a distance proportional to depth, and this lateral shift is in the other direction for the other eye. Though confocal microscopes frequently have the capability to perform this operation, it is rarely used, partly because it generally introduces an unacceptable delay between exposure and image display.

The problem of producing real time stereoscopic images is particularly great at the cutting edge of high resolution light microscopy using techniques that reduce the diameter of a scanned spot by eliminating fluorescence at the periphery of the spot before significant fluorescent emission (Hell and Wichmann, U.S. Pat. No. 5,731,588, Baer, U.S. Pat. Nos. 5,777,342, 5,866,911, 5,952,668 and 6,259,104 and 6,903,347 which are incorporated herein by reference.). In practice, these techniques have been found to produce photobleaching, which has limited the exposure possible for a specimen, so that techniques requiring many exposures are difficult to implement. Alternative techniques that reduce the size of an excited or excitable spot by using special properties of dyes and proteins that can optically switch between fluorescent and non fluorescent states require long dwell times per pixel, again making producing of many images from a specimen difficult.

Providing a microscope, which combined real time high depth-of-field imaging and stereoscopic visualization with resolution beyond the Abbe limit has remained a long standing unfulfilled need.

OBJECTS AND ADVANTAGES

One object of the present invention is to extend the effective depth of focus of a microscope without requiring focusing at different depths.

Another object, when the present invention is applied to resolution enhancement techniques that reduce excitation in the peripheral parts of a scanned spot, is to provide resolution improvement that remains substantially constant at different distances from the plane of focus.

Another object is to allow construction of a stereoscopic pair for an image in a high magnification scanning microscope with just a single scan.

Another object is to allow production of real time stereoscopic pair images at unprecedented magnification and resolution.

Another object is to allow cues such as defocus and reduced intensity with distance from focal plane to contribute to the illusion of stereopsis.

Another object is to produce a real time stereoscopic image where the magnification is substantially invariant of depth.

SUMMARY OF THE INVENTION

The forgoing objects are achieved and the foregoing problems are solved in an illustrative embodiment of the invention, applied specifically to the field of scanning fluorescence microscopy. In scanning microscopy, a spot or line is scanned laterally over the focal plane of a specimen in two or one dimensions respectively, to sample the fluorescence of the different parts of the field of view. In the present invention, first the spot is elongated into a narrow needle shaped illuminated region, oriented so it passes through different depths of the specimen, and also is inclined with respect to the optical axis of the microscope. This region will sometimes be referred to in this description as a "tilted luminous needle." This tilted needle together with another needle tilted in the opposite direction with respect to the optical axis, is then scanned laterally over the specimen. Light collected from the regions illuminated by these two needles is detected by separate channels and used to form images for the left and right eyes.

In more complex embodiments of the invention, the diameter of the tilted needles is reduced by the quench surround or STED microscope resolution enhancement techniques as described in Hell and Wichmann, U.S. Pat. No. 5,731,588 and Baer U.S. Pat. Nos. 5,866,911, 5,952,668, and 6,259,104, allowing construction of a real time, stereoscopic image of the specimen, combining ultrahigh depth-of-field and ultra high resolution.

BRIEF DESCRIPTION OF THE DRAWINGS

FIG. 6 is a cross-sectional view showing an embodiment of the present invention, where two elongated and scanned regions of the specimen are tilted in opposite direction, to generate effective stereoscopic imaging of the specimen.

FIG. 7 is a cross-sectional view of the system for generating pinholes which produce the tilted needles required in a STED embodiment of the present invention.

FIG. 8 shows a schematic cross sectional view showing the positions of the images of the pinholes at different places in the device of FIG. 6.

MODES FOR CARRYING OUT THE INVENTION

Figure 1:
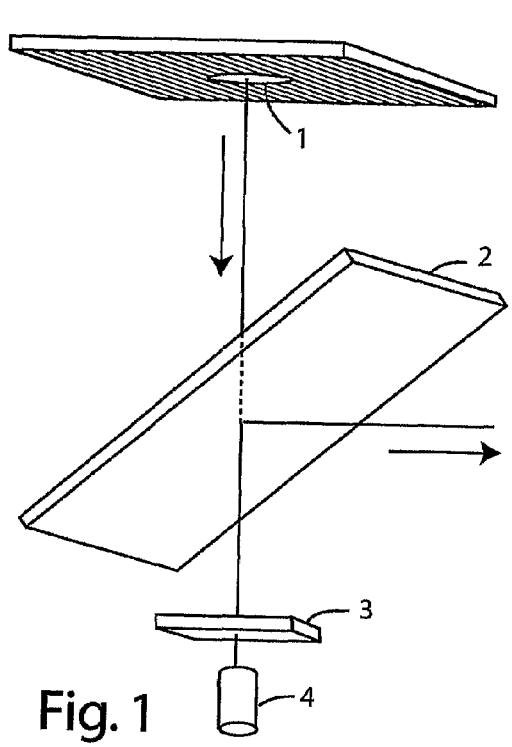
FIG. 1 is a three-dimensional view of a conventional confocal or multiphoton microscope.

The present invention can best be seen in relationship to a conventional beam-scanned laser confocal microscope and a quenching sharpened scanning fluorescence microscope, referenced above. The conventional beam-scanned confocal microscope (Baer, U.S. Pat. No. 3,705,755) is shown in FIG. 1, where light emanating from a pinhole 1, illuminated by a convergent laser beam from above (not shown) passes through a dichroic mirror 2, then through a beam scanning means to enter objective 4, which focuses the light on a spot in the specimen (not shown). Light returning from the specimen is reflected from dichroic mirror 2 to be focused on a confocal pinhole (not shown) and the light passing through that pinhole is detected and used to determine the brightness and/or color of a point in the final image corresponding to the illuminated point in the specimen.

Figure 2:
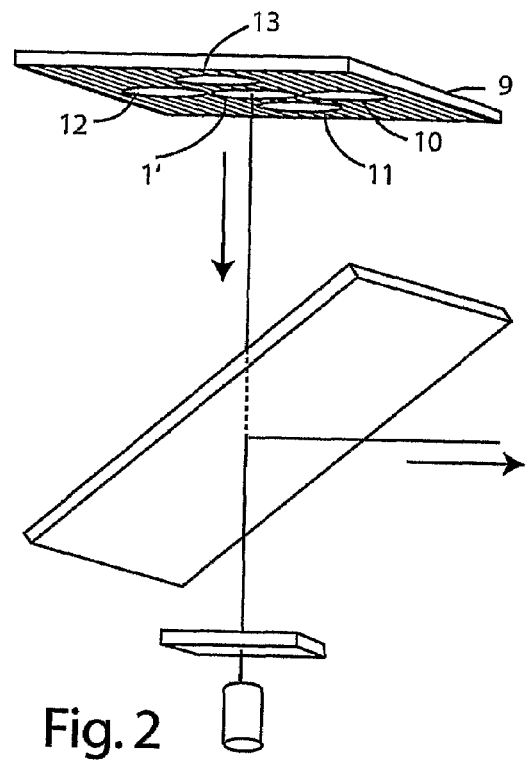
FIG. 2 is a three-dimensional view of a quench surround or STED microscope.
Figure 10:
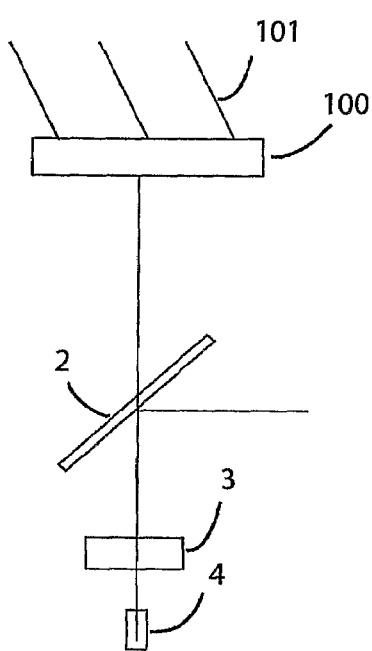
FIG. 10 is an embodiment of the present invention where a hologram implements the production of a luminous needle parallel to the optical axis, for production of depth enhanced images by scanning.
Figure 11:
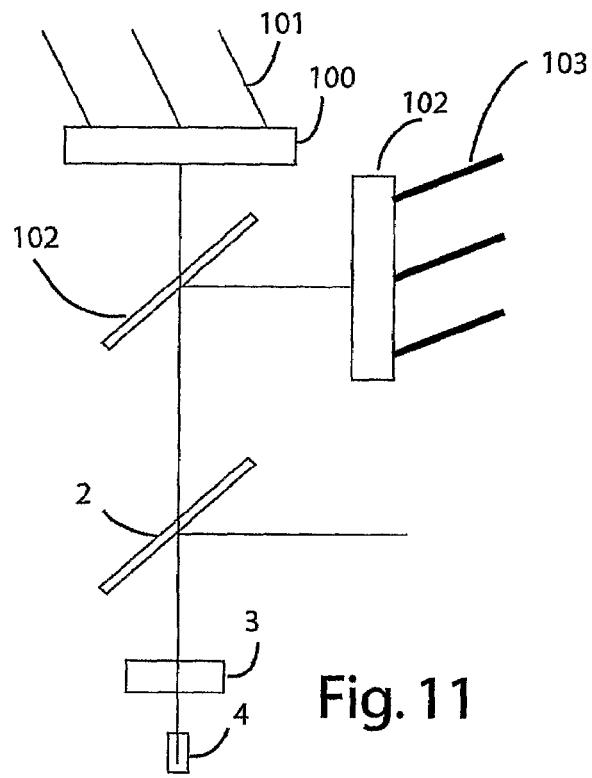
FIG. 11 is an embodiment of the present invention employing two holograms, one for producing the necessary pattern for excitation and the other for producing the necessary pattern for quenching.

The quench-sharpened or STED version of that beam scanned confocal microscope instrument, which can be understood with reference to the device shown in FIGS. 10 and 11 of U.S. Pat. No. 5,952,668 is shown in FIG. 2. Pinhole cluster 9 contains 5 pinholes, 1', 10, 11, 12 and 13. The excitation laser (not shown), which is focused on excitation pinhole 1', emits pulses of around a few hundred femtoseconds, and that light from that pulse which passes through pinhole 1' is focused onto a spot in the specimen to excite fluorescence in a fluorophore. Shortly after the end of the excitation pulse, a quenching laser pulse of several picoseconds to several hundred picoseconds is focused (from above in FIG. 2) onto quenching pinholes 10, 11, 12 and 13 which surround the excitation pinhole 1'. The important properties of the quenching pulses is that the light emanating from opposite pinholes 10 and 12 is 180° out-of-phase and the light emanating from other pair of opposite pinholes 11 and 13, is also 180° out-of-phase, yet the light from the pair 10 and 12 cannot interfere with light from the pair 11 and 13. As discussed in U.S. Pat. No. 5,952,668, this may be accomplished by introducing a phase delay of 0°, 90°, 180° and 270° for the light emanating from pinholes 10, 11, 12 and 13 respectively. The pinholes 10, 11, 12 and 13 are spaced so their centers are approximately 2.3 optical units from the optical axis, and with this geometry, they form a doughnut shaped intensity distribution in the focal plane, with a theoretically zero intensity in the center, and with intensity that quickly rises with distance from that central point. That will produce optimal quenching of the excited spot for maximal resolution improvement.

Figure 3:
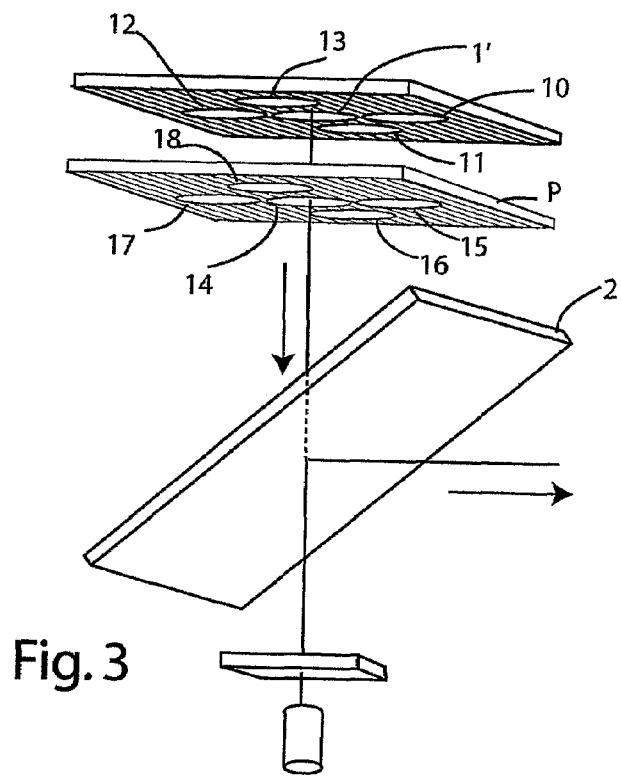
FIG. 3 illustrates a method to extend the depth of field of the microscope shown in FIG. 2.

FIG. 3 shows how the spots generated in the specimen by the device of FIG. 2 can be depth extended into luminous needles generally parallel to each other and to the optical axis. In addition to light emanating from pinholes 1', 10, 11, 12, and 13, light also emanates from virtual pinholes 14, 15, 16, 17 and 18, located in a plane P parallel to the plane of the pinholes 1', 10, 11, 12, and 13. These virtual pinholes are images of pinholes or light sources, and light emanates from them, but at the same time, light from pinholes 1',10, 11, 12, and 13 passes unobstructed through the plane of virtual pinholes 14, 15, 16, 17 and 18. In this disclosure, the term "pinhole" is interpreted broadly to include, for example, the end of an optical fiber, or the focus or a focused collimated beam or the image of the end of a fiber or a literal pinhole.

Pinhole 14 is spaced from pinhole 1' so that it is focused below the spot focus of pinhole 1', such that the center of the focus of the light from pinhole 14 is within the central maximum of the focus of the light from pinhole 1'. The phase of the light emanating from pinhole 14 is adjusted so that the phase at the central point of its image in the specimen is the same as the phase of the light from the focus of pinhole 1' at that point. Generally meeting these conditions, the spacing between pinholes 1' and 14 is adjusted to create a combined focus which is very elongated in the z axis. Substantially meeting the same phase conditions, the foci of light from the combination of the light from pinholes 10 and 15 forms a similarly shaped central maximum elongated in the z dimension, and the same is true for the combination of light from pinholes 11 and 16, the combination of light from pinholes 12 and 17 and the combination of light from pinholes 13 and 18.

The phase relationships between the needle shaped volumes of excitation light and quenching light produced by the device in FIG. 3 are such that the light from quenching needles on opposite sides of the excitation needle cancel at the central axis of the excitation needle, and light from one pair of opposite needles does not interfere with light from the other pair of opposite needles. This situation insures that the "doughnut" of the STED microscope is stretched in depth into volume illuminated by quenching light, having an extended zero intensity axis. This structure is called here, somewhat loosely, a "hollow needle of quenching light" even though, as shown in the simulation in FIG. 9, the only part that is truly needle like is the central core. This zero intensity central axis is made to coincide with the needle shaped region of excitaiton light, thereby reducing its diameter along its length. The result is that following quenching, the needle shaped volume of the specimen excited by the excitation light is constricted into a much narrower diameter needle shaped volume.

Figure 4:
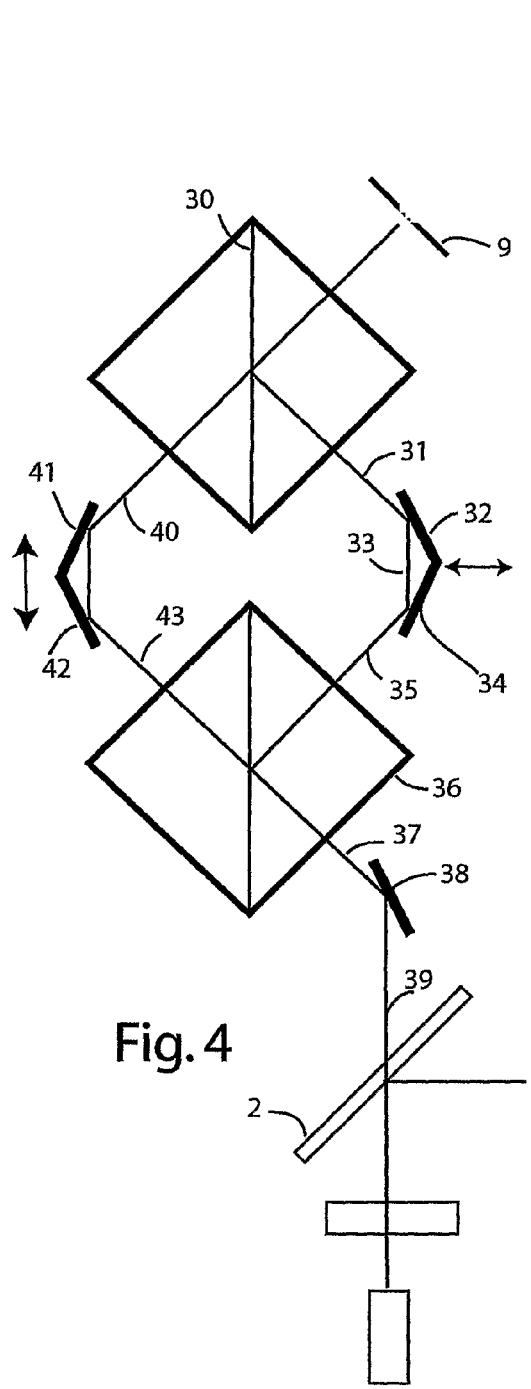
FIG. 4 is a cross-sectional view showing how the device illustrated in FIG. 3 might be implemented by means of beam splitting cubes and mirrors.

FIG. 4 shows an optical arrangement for creating the device schematized in FIG. 3. Pinhole cluster 9 is the same as is illustrated in FIGS. 2 and 3. Excitation light leaving pinholes 1' (not labeled) is partially reflected by beam splitter 30 to ray 31, which is reflected by mirror 32 to ray 33, which is reflected by mirror 34 to ray 35, which after partial reflection by beam splitter 36 becomes ray 37 which after reflection by mirror 38 is directed to the beamsplitter 2, identical to the beamsplitter 2 from FIG. 3. That portion of the light from pinhole 1' that is transmitted by beamsplitter 30 becomes ray 40, which after reflection by mirrors 41 and 42 becomes ray 43, which after transmission through beamsplitter 36 is superimposed with ray 37. The light in ray 37 arises from two virtual mirror images of pinhole 1', produced by multiple reflections. One of these virtual images results from the component transmitted by beamsplitter 30 and the other virtual image results from the component reflected by beamsplitter 30. If the beam splitting surfaces of beam splitters 30 and 36 are coplanar and the mirrors 32 and 34 are symmetrically placed relative to that plane with mirrors 41 and 42, then these two virtual images of pinhole 1' coincide. Mirrors 32 and 34 are moved horizontally as a rigid unit, and cause a change in the path length of the component of light from pinhole 1' reflected by beamsplitter 30, without causing any lateral shift. This causes an axial movement in the virtual image of pinhole 1' from the component light from pinhole 1' reflected by beamsplitter 30. Since the virtual image of pinhole 1' from the component of light transmitted by beamsplitter 30 does not change, this movement of mirrors 32 and 34 causes an axial displacement between the two virtual images of pinhole 1'. Mirrors 41 and 42 move vertically as a rigid unit, and control the lateral displacement between the two virtual images of pinhole 1'. Therefore by movement of mirrors 41, 42, 32 and 34, it is possible to adjust the relative positions of the two virtual images of pinhole 1' in both the axial and one lateral dimension. Movement of these mirrors also produces the same axial and/or lateral displacement of the virtual images of pinholes 10, 11, 12, and 13, so that the pinholes on cluster 9 have the same relative positions in both virtual images.

In the device shown in FIG. 4, the transmitted component of beam 35 and the reflected component of beam 43 from beamsplitter 36 are wasted. Assuming the beamsplitter reflects and transmits 50%, this wasted light represents half of the laser output. The embodiment in FIG. 5 utilizes this wasted light, by producing two needles of excitation in the specimen. The ray 50, that was wasted in the embodiment shown in FIG. 4, is directed on the specimen by means of an elliptical mirror 51 and a plane mirror 52 to contribute to creating an image of the pinhole cluster near point 53 in real image plane 55 (which is shown much closer to the beamsplitter 2 than the real image plane in the device of FIG. 4, which is at the pinhole cluster 9). The light including ray 37 creates another image of the pinhole cluster near point 54, laterally displaced from point 53 in plane 55. The purpose of the relay system, including the elliptical reflector 51, is to allow the images of the pinhole clusters to be close to each other in the real image plane 55. The light from these pinhole cluster images is focused on the specimen by objective 4 and the fluorescent emission from the specimen is collected and focused by objective 4, descanned by scanner 3, and reflected by dichroic beamsplitter 2 onto two separate detectors 56 and 57. The sensitive areas of these detectors are not as narrow as confocal pinholes, since they must accept light from a larger region from the specimen, and they improve their collection efficiency by accepting emitted light scattered over a narrow angle. Because the process of quench sharpening and two-photon excitation both avoid out-of-focus light, there is no need for a narrow confocal detector pinhole. The outputs from detectors 56 and 57 produce two different raster scanned images. By laterally shifting one of these images with respect to the other, they can be superimposed and added to produce a composite image.

It is possible that these two images can have different functions, for example being made with different polarizations, or being focused to slightly different depths of the specimen. In the present invention, these two images form needles that are tilted in opposite directions with respect to the optical axis, to create left and right stereoscopic views, as in the embodiment of the invention shown in FIG. 6, which shows the preferred form of the present invention.

Figure 5:
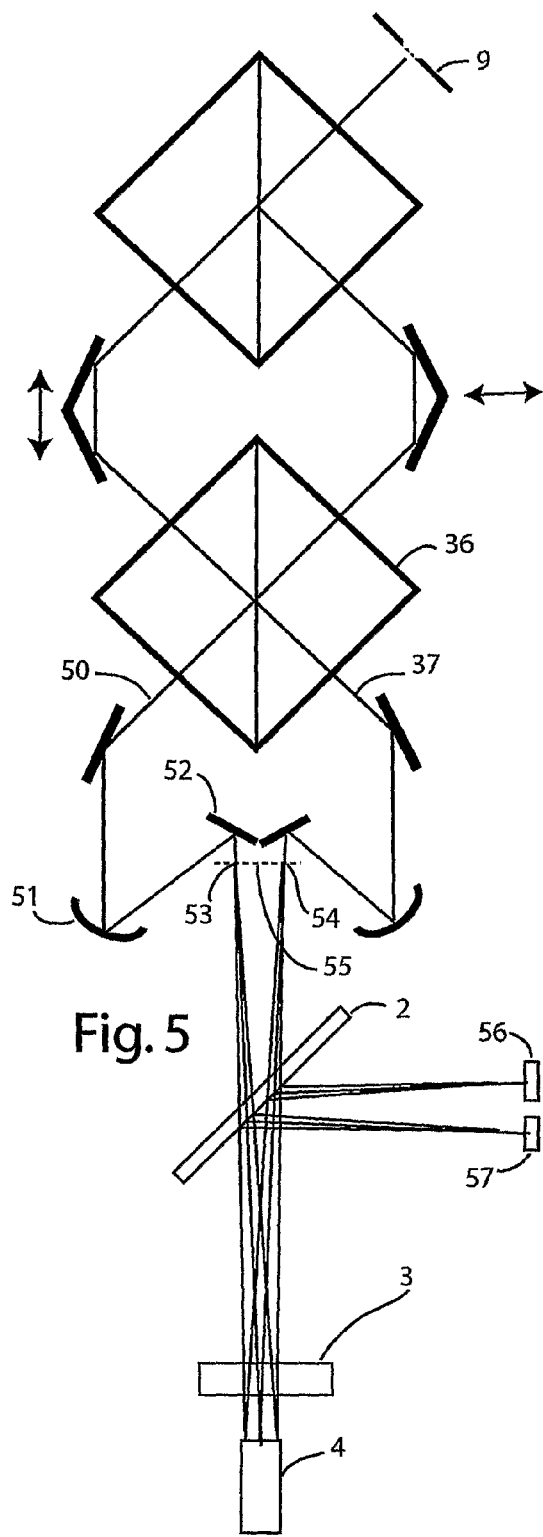
FIG. 5 is a cross-sectional view showing a device similar to that shown in FIG. 4, but simultaneously scanning two regions of the specimen.

The devices shown in FIGS. 4 and 5 produce, after quenching, effectively illuminated volumes shaped like long narrow cylinders, parallel to the optical axis, such that these cylinders flare out at the top and bottom. The shape is roughly like the neck of an hourglass with an elongated neck. Because the flared out region of this hourglass shape fails to restrict the fluorescence, any initially excited points in this volume will not only be out of focus, but will contribute a disproportionate input to the detector. This problem, which could be called the "flaring problem" can lead to a substantial resolution loss of the image. In addition to providing an extended depth-of-field, the embodiment shown in FIG. 6 addresses this flaring problem since for most regions excited by the needle of excitation light, quenching remains restricted to the same narrow diameter even at substantial distances from the central plane of focus.

In the device shown in FIG. 6, which embodies the present invention, two separate pinhole clusters supply the light input; light from some of the pinholes enters beamsplitter from face 63 and light from other pinholes enters it from face 64. The grids 61 and 62 represent the positions of the images of the pinholes in the specimen, with the depth or z axis shown, and the other dimension, x, representing a lateral dimension. The unit in the grids represents one dimensionless optical unit, which is approximately equal to 100 nm with a quenching wavelength of 760 nm and an objective NA of 1.25. In grids 61 and 62, the solid dots such as 10' represent sources of quenching radiation within the cross-sectional plane, the hollow dots such as 13' represent sources of quenching radiation in planes on either side of the cross-sectional plane, on both sides of it, and 2.5 units away from it, and the square dots such as 1' represent sources of exciting radiation.

FIG. 7 shows how the configuration of pinholes shown in FIG. 6 may be implemented by light emanating from optical fibers and collimated by small positive lenses. FIG. 7A is a cross-sectional view in the plane shown by grid 62. Light from optical fiber 76, at the quenching wavelength, is split by beam splitter 77 into two diverging beams, one of which is reflected by mirror 78 onto positive lens 79, of a focal length so that the end of fiber 76 is at a focal point of lens 79 (after reflection by mirror 78 and the reflecting surface in beam splitter 77). Lens 79 therefore collimates the light diverging from fiber 76 into a generally parallel beam, and this beam is directed at beam splitter 36. The entire circular cross section of lens 79 functions as pinhole 12' of grid 62. Similarly lens 80 collimates the other beam diverging from beam splitter 77, to produce a generally parallel beam. The circular cross section of lens 80 functions as pinhole 10' of grid 62. Optical fiber 81, which conducts excitation light, emits a diverging beam that is collimated by lens 82, which functions as pinhole 1' of grid 62. By translation of mirror 78 in a direction perpendicular to its surface, the phase relationship between the optical fibers 81 and 83 is adjusted to cause the light spreading from the images of pinholes 12' and 10' in the specimen to exactly cancel at the midpoint between the central points of the images of these lenses in the specimen. By introducing a rotatable glass plate (not shown) between mirror 78 and lens 79, it would be possible to insure that the cancellation takes place at two separate wavelengths, for achromatic phase delay.

FIG. 7B is a cross sectional view through line 75 of grid 62 but in a plane perpendicular to the plane of the cross section in FIG. 6. Quenching light diverging from the end of fiber 83 is split by beam splitter 84, and one of the beams emerging from beam splitter 84 is reflected by mirror 85 to positive lens 86, which collimates the quenching beam. Lens 86 functions to implement pinhole 13' of FIG. 6. (This pinhole 13' is above the plane of the illustration in FIG. 6, but shown in its projection on the plane.). The quenching light in fibers 81 and 83 has a constant phase relationship, and in fact these fibers could be derived from a single parent fiber via an achromatic fiber optical beam splitter, which also produces two additional quenching beam optical fibers to supply optical configurations analogous to those shown in FIG. 7 to implement the pinholes shown (unlabeled) in grid 61 of FIG. 6. By adjusting the relative phase delay between the light leaving fiber 81 and fiber 83, perhaps by longitudinally translating fiber 83, it is possible to create a situation where the phase of light from the images of the pinholes reaches the point in the specimen midway between their respective images with delays of 0°, 90°, 180° and 270° from pinholes represented by lenses 79, 86, 80 and 87 respectively. This is an advantageous configuration of phases, as discussed in U.S. Pat. No. 5,952,668.

At point 65, on the path where light exits beamsplitter 36, the mirror image of the pinholes shown grid 61 are superimposed with directly transmitted light from the pinholes in grid 62, to be in the positions shown in the grid A in FIG. 8. Similarly grid B in FIG. 8 shows the two superimposed sets of pinholes as seen from point 66.

The pattern of light at point 65, schematized by the diagrams in grids A and B of FIG. 8, when imaged in a specimen by focusing means such as elliptical reflector 51 in FIG. 5, will produce a needle-like cylinder of quenching light that is tilted with respect to the optical axis, and where the image of the two spots of excitation light fall off substantially before the needle has flared out. Light at point 66 could be imaged on the specimen to produce a similar needle, tilted in the opposite direction, and the points illuminated by these needles imaged on separate photodetectors to create stereoscopic images. However in the device of FIG. 6, there is a second beam splitting prism 70, which superimposes a reflected image of the pinholes schematized in grid A in FIG. 8, with a shifted image of the pinholes schematized in grid B in FIG. 8, to produce a pattern of pinhole images schematized in grids C of FIG. 8. The pattern in FIG. 8D is produced by the image of pinholes as in FIG. 8A, superimposed with a shifted and reflected image of the pinholes in FIG. 8B.

Figure 9:
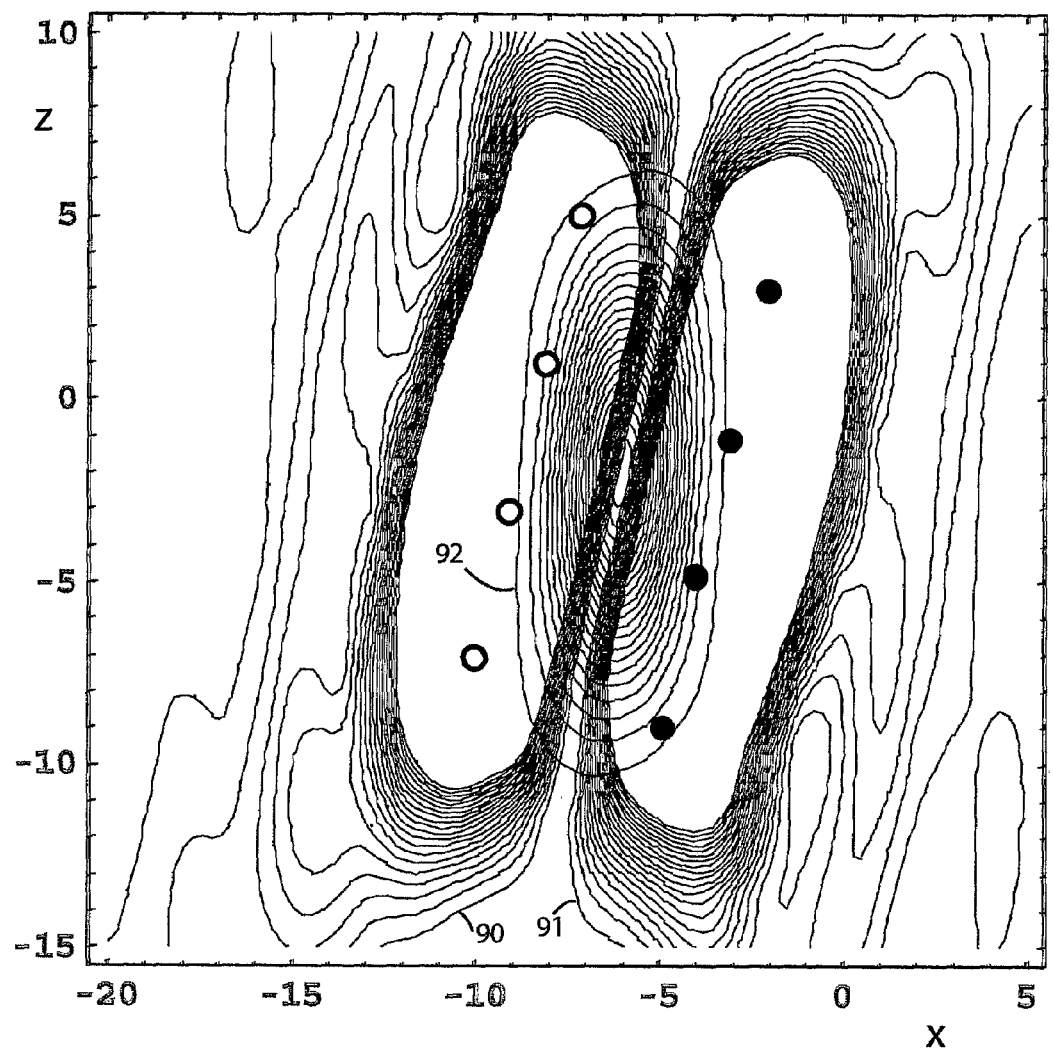
FIG. 9 is a computer generated plot of isophotes of the excitation and quenching light in the specimen produced by the device of FIG. 6.

FIG. 9 shows computed isophote contours of the intensity distribution in the specimen of the pattern shown in FIG. 8 D. The round dots represent images of the pinholes. The isophotes 90 and 91 represent 5% of the maximum intensity at the central point of each pinhole image. The scale is in dimensionless optical units, and for a quenching beam wavelength of 760 nm and a 1.25 NA objective, each unit equals about 100 nm. If the quenching beam power is raised to the level where at the intensity of the isophotes 90 and 91, half the excited fluorophores are deexcited, then the FWHM of the needle, post quenching, is in the range of 25 nm. Though not shown in this figure, the cross-section of the needle is roughly circular. The isophote 92 represents 5% of the maximum of an I2 (intensity squared) distribution of the excitation beam. When the fluorophore is two-photon excited, at below saturation, the isophote 92 represents the point when only 5% of the fluorophores are excited relative to the central maximum, and at that point the FWHM of the needle has expanded to just 50 nm. Between these 5% endpoints, the length of the needle is about 1,600 nm. In practice, two such needles, tilted in opposite directions, would be projected simultaneously in the specimen, and light from them would be recorded on two separate photodetectors, such as detector 56 and 57 in FIG. 5.

The tilted needle-shaped intensity distribution shown in FIG. 9 may be achieved in other ways. For example, rather than creating a pattern of pinholes and imaging it in the specimen, a hologram of this pattern could be made, and a holographic image of the intensity pattern shown in FIG. 9 could be projected into the specimen. This hologram could be produced either by means of light from an optical configuration shown in FIGS. 6 and 7, interfering with light from a reference laser beam, or it could be generated by a computer.

Several alternative holographic embodiments of the present invention will now be described in more detail. FIG. 10 shows a simple microscope that does not employ resolution enhancement by STED, and which generates a luminous needle of excitation light in the specimen by an illuminated hologram. The dichroic mirror 2, beam scanner 3 and objective 4 are the same as the confocal microscope shown in FIG. 1. Instead of the excitation pinhole 1 of FIG. 1 is a hologram 100, which when illuminated by laser beam 101, generates a holographic image of the absent excitation pinhole 1, When so illuminated, hologram 100 also creates holographic images of other at different depths, so that excitation light from all these holographic pinhole images are focused by objective 4 to points on a line in the specimen, so that the points are close enough to each other, and have the appropriate phase relationships, so that the combination creates a luminous needle, just as in which will be projected by objective 4 to various points on a line in the specimen, so as to create a luminous needle, as in earlier described embodiments of the present invention. The holographic images of the pinholes can have different lateral positions, so that the luminous needle created in the specimen is tilted, like the needles of excitatory light created by the embodiment shown in FIG. 6. Furthermore the there can be two sets of such holographically generated pinhole images, arranged to create in the specimen two luminous excitation needles, tilted in opposite directions, as in the device shown in FIG. 6.

The device of FIG. 10, with a hologram in place that created two oppositely tilted needles of excitation light, could provide a very useful embodiment of the present invention, even though it lacked the resolution enhancement provided in the device of FIG. 6 by surrounding the excitation needles by hollow needles of quenching light. It would be necessary to provide two channels of light detection, such as is provided by light detectors 56 and 57 in the device of FIG. 6, to generate left and right stereoscopic images, as the scanning means 3 simultaneously scans both of the tilted needles over the specimen. In the imaging process, in order to increase contrast and decrease background illumination, the laser beam 101 could be a repetitively pulsed femtosecond beam, such as is produced by a mode-locked Ti-Sapphire laser, which could excite fluorophores in the specimen by multiphoton absorption.

The hologram 100 could be made by exposing it to the superimposed light from the beam 101 and a laser light, coherent with beam 101 and convergent to a point at position that in a confocal microscope would be occupied by pinhole 1, as is well known in the art of holography. The holographic images of the other excitation pinholes could be similarly encoded in the hologram by subsequent exposures of the hologram to the intersection of beam 101 and beams coherent with beam 101 and convergent on the various other pinhole positions. Then the hologram could then be developed and mounted on the microscope. Alternatively hologram 100 could be exposed by well know processes of using a computer to calculate the pattern of density and/or refractive index variations in an actual holographic storage medium, and then these variations would be written in the medium pixel by pixel to simulate the exposure process.

Outfitted with a femtosecond laser to generate beam 101 and a pair of detector channels such as 56 and 57, to measure light emanating from the regions of the specimen occupied by the two oppositely tilted excitation needles during scanning, the device of FIG. 10 could create a microscope that could generate real time stereoscopic images of high depth of field at the same magnifications currently achieved by multiphoton microscopes.

Because high magnification microscope objectives are corrected for spherical aberration at just one focal distance, the process of exposure of the hologram could include spherical aberration correction for the imaging away from the primary focal plane, Furthermore the process of making the hologram could generate two tilted needles of excitation light, thereby implementing an embodiment of the present invention which lacks the high resolution of the embodiment shown in FIG. 6, but is far simpler, since it only requires an excitation laser. There would have to be two detectors for light from the two tilted needles, just as in the device of FIG. 6, Considerations of complexity of the apparatus constrains devices like that shown in FIG. 6 to form the luminous needles with just a few summated pinhole images, for example just 4 summated images per needle in the device of FIG. 6. However, there is no such constraint with the use of holograms, so the tilted needles could be made as long as desired, for whatever depth-of-field was desired, and could simulate with single scans z-stacks with hundreds of images at different depths.

Simulating a STED device such as shown in FIG. 6 by holograms requires the hologram to be able to create both solid needle(s) of excitation light and also hollow needles of quenching light. A simple solution is to employ separate holograms for excitation and quenching. In the device shown in FIG. 11, in common with the device of FIG. 10, hologram 100 creates multiple images of excitation pinholes when illuminated by beam 101 of excitation light, In addition, a second hologram 102 creates the multiple images of the quenching pinholes required to generate the hollow quenching needles when illuminated by the quenching beam 103. The wavefronts from the two holograms are combined by beamsplitter 104.

Figure 12:
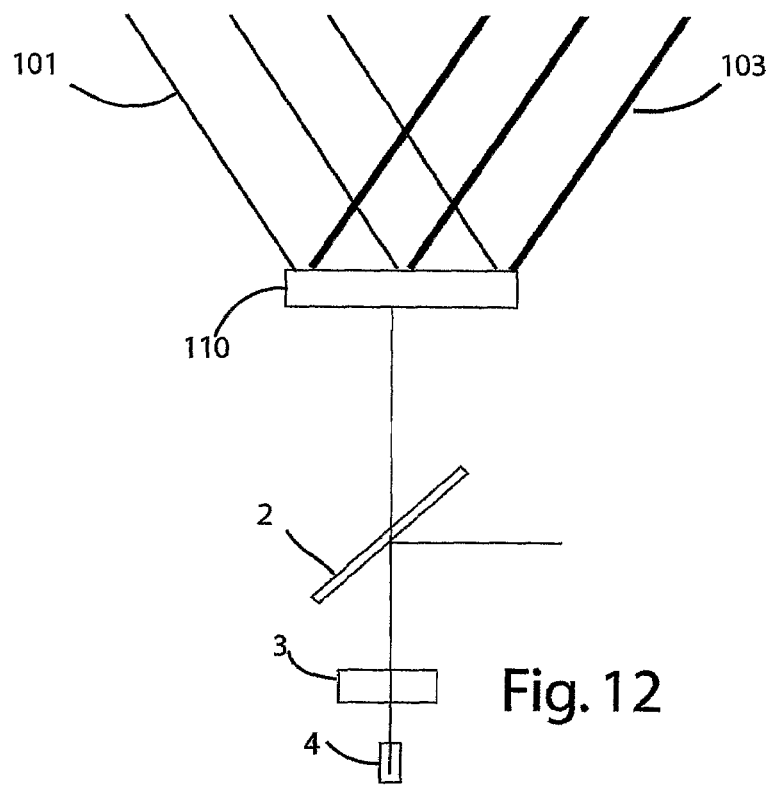
FIG. 12 is an embodiment of the present invention where a single volume hologram provides the necessary pattern for both excitation and for quenching.

FIG. 12 shows how a single hologram could generate both excitation needles and hollow quenching needles. Hologram 110 is a volume hologram, and the local density/phase variations are stored in a three-dimensional volume. Such holograms are sensitive to the direction of the readout laser beam, so beams 101 and 103 could each generate their respective required images. These examples show just a sample of how the rich field of holography could be applied to the implementation of the present invention.

In deciding the best mode, a discrete optical device such as shown in FIG. 6 has some advantages while a holographic embodiment such as shown in FIGS. 10, 11 and 12 has others. The discrete device can use light very efficiently, and by carefully applying antireflective coatings to the surfaces, the contrast can be very high, something important in STED microscopy, since the darkness of the zero point of the "doughnut" (or in this case the "hollow needle") is related to the resolution attainable with a given STED beam power. Furthermore the properties of a discrete optical instrument can be well predicted by mathematical simulation. On the other hand, as the art of holography yields ever more efficient holograms, with less and less spurious scattered light, the appeal of the versatility and simplicity of the holographic arrangements becomes paramount. Our inclination is to consider the device of FIG. 6 as the best mode in the short term, and then attempt to equal and then surpass its performance with holographic embodiments. It should be noted, that sometimes diffraction elements that are not strictly called holograms can perform similar functions to the hologram described herein, and as such the term hologram is intended to encompass such diffraction elements.

Several different methods have been proposed for creating a doughnut shaped intensity distribution for STED or quench surround resolution improvement. Virtually any of these methods could be adapted for the present invention of creating high depth-of-field imaging, by including means such as the beam splitter prism 36, to create multiple images of said doughnuts at different depths.

The embodiment of the present invention shown in FIG. 6 generated needles formed from four collinear spots, in the specimen. However by including another beam splitting prism stage, similar to prism 70, and its associated mirrors, these four pairs could be duplicated to create eight pairs and so on. In this way extremely high depths of field can be generated, using a discrete optical arrangement, and as has been pointed out, such expansion of the depth could be carried out with holographic embodiments without introducing added complexity. However since each stage of spot duplication introduces a chance for additional scattering, with the resulting lowered contrast in the specimen, and a corresponding loss of resolution, the arrangement shown in FIG. 6 might be optimum, and additional depth-of-field could be produced by refocusing the specimen, making additional scans and using Z-summation.

The beam splitters in the discrete optical implementations described could be replaced by alternatives such a polarizing beam splitters, with compensating half wave plates, or by pellicles, in an effort to reduce scattering or improve light transmission and reflection efficiency.

Since the embodiment shown in FIG. 6 is called to focus spots of light at different depths of the specimen, while high NA objectives are optimally corrected for spherical aberration only at one depth, spherical aberration correcting elements could be introduced into the beam, for example at point 66, so that each set of pinhole images in the specimen could have spherical aberration separately corrected for its particular depth, as has been discussed for the holographic embodiments.

There is highly developed art for automatically interpreting stereoscopic pairs of images to compute the three-dimensional coordinates of the image points. It is imagined that as sophisticated forms of such methods become available to process in real time the data stream from the photodetectors such as detectors 56 and 57, a microscope embodying the present invention could have a real time output corresponding to the equivalent of N stacked two dimensional sections, at the maximum frame rate of the microscope.

These synthesized stacked two dimensional Z sections, could then be accessed just as in confocal microscopy three dimensional reconstruction programs, for example for virtual rotation of the specimen, or to produce a cross section at any desired tilt and position.

In the embodiments of the present invention discussed in this description, two tilted needles were simultaneously scanned over the specimen. However it would be possible to perform this process sequentially, with images for the left and right eyes collected during alternate scans. Furthermore it is possible to have needles of several different degrees of tilt scanned, since the data collected could be used to provide input to some forms of stereoscopic displays that require several images of a subject, viewed from several angles. The embodiments have described microscopic visualization, but the principles could also be applied for imaging at much larger scales. Thus the breadth of the present invention should not be limited by the embodiments described, but rather by the following claims.

What is claimed is:

1. In a microscope, said microscope having an optical axis, a method for producing stereoscopic images of a specimen, comprising the steps of:
    illuminating a first needle-shaped volume in the specimen, said volume having an axis that is tilted with respect to said optical axis,
    illuminating a second needle-shaped volume in the specimen, said volume having an axis that is tilted with respect to said axis of said first needle shaped volume,
    scanning said first and second volumes relative to said specimen,
    measuring the light emanating from said volumes during said scanning,
    forming a first image of said specimen based on the measurements of light emanating from said first volume, and
    forming a second image of said specimen based on measurements of light emanating from said second volume, such that said second image is formed currently with the formation of said first image.

2. The method of claim 1, wherein said specimen contains fluorescent molecules, or molecules capable of being switched to and from a fluorescent state, and wherein said first needle-shaped volume is illuminated by a wavelength able to create an excited state in said molecules.

3. The method of claim 2, comprising the additional step of generating a first cylindrical shaped volume, having a central axis, illuminated by a wavelength able to reduce the ratio of said molecules in said excited state to said molecules not in said excited state, said cylindrical shaped volume having a lower intensity on its central axis than away from its central axis, and such that said central axis substantially coincides with the axis of said first needle-shaped volume.

4. The method of claim 2 wherein said volume is illuminated by a wavelength able to excite said molecules by multiphoton absorption.

5. The method of claim 1, wherein the steps of illuminating said first and second needle-shaped volumes in said specimen occur simultaneously.

6. The method of claim 1, comprising a hologram.

7. The method of claim 1, wherein the step of illuminating said first needle-shaped volume comprises the additional steps of generating a plurality of light sources from a single source by passing light from said single source through an optical assembly comprising at least one partially reflecting surface, to create a plurality of images of said single source and focusing the light from said plurality of light sources to different locations along the axis of said first needle shaped volume.

8. The method of claim 7, wherein the sources in said plurality of sources are noncontiguous.

9. The method of claim 1, wherein the axis of said first needle-shaped volume makes an angle of less than 45° with said optical axis.

10. In microscope for imaging a specimen to produce stereoscopic images of said specimen, said microscope having an optical axis,
    an optical assembly to illuminate a first needle-shaped volume in the specimen, said volume having an axis that is tilted with respect to said optical axis,
    an optical assembly to illuminate a second needle shaped volume in the specimen, said second needle-shaped volume having an axis tilted with respect to said axis of said first needle-shaped volume,
    a scanner to scan said first and second volumes relative to said specimen,
    photosensitive device to measure the light emanating from said volumes during said scanning,
    apparatus to form a first image of said specimen based on the measurements of light emanating from said first volume, and
    apparatus to form a second image of said specimen based on measurements of light emanating from said second volume, such that said second image is formed currently with the formation of said first image.

11. The microscope of claim 10, wherein said specimen contains fluorescent molecules, or molecules capable of being switched to a fluorescent state, and wherein said first needle-shaped volumes is illuminated by a wavelength able to create an excited state in said molecules.

12. The microscope of claim 11, comprising an optical assembly adapted to illuminate a first cylindrical shaped volume, having a central axis, wherein the wavelength of illumination of said cylindrical shaped volume is able to reduce the ratio of said molecules in said excited state to said molecules not in said excited state, wherein the intensity of said cylindrical shaped volume is lower on its central axis than away from its central axis, and such that said central axis substantially coincides with the axis of said first needle-shaped volume.

13. The microscope of claim 10, wherein said first and second needle-shaped volumes in said specimen are illuminated simultaneously.

14. The microscope of claim 10, comprising a hologram.

15. The microscope of claim 10 wherein said needle-shaped volumes are illuminated by a wavelength able to excite said molecules by multiphoton absorption.

16. The microscope of claim 10, wherein the optical assembly illuminating said first needle-shaped volume comprises at least one partially reflecting surface to form light from a single source to create a plurality of images of said single source, and elements to focus light from said plurality of images to different locations along the axis of said first needle-shaped volume.

17. The microscope of claim 16 wherein the sources in said plurality of sources are noncontiguous.

18. The microscope of claim 10, wherein the axis of said first needle shaped volume makes an angle of less than 45° with said optical axis.

19. In optical apparatus to produce stereoscopic images of an object, said apparatus having an optical axis,
    an optical assembly to illuminate a first needle-shaped illuminated volume at said object, said volume having an axis that is tilted with respect to said optical axis, an optical assembly to illuminate a second needle shaped volume having an axis tilted with respect to said axis of said first needle shaped volume, a scanner to scan said first and second volumes relative to said object, a photosensitive device to measure the light emanating from said volumes during said scanning, an optical assembly to form a first image of said object based on the measurements of light emanating from said first volume, and an optical assembly to form a second image of said object based on measurements of light emanating from said second volume, such that said second image is formed currently with the formation of said first image.

20. The apparatus of claim 19, wherein said first and second needle-shaped volumes in said specimen are illuminated simultaneously.

* * * * *